(12) United States Patent
Glas (10) Patent No.: US 12,357,585 B2
(45) Date of Patent: Jul. 15, 2025

(54) CANNABIGEROL AND PHARMACEUTICAL COMPOSITIONS COMPRISING CANNABIGEROL FOR USE IN THE TREATMENT OF INSOMNIA

(71) Applicants: AKASHA CORPORATION, Anguilla (AI); LIV INNOVATION SA, Lugano (CH)

(72) Inventor: Ronald Johannes Glas, Lugano (CH)

(73) Assignees: AKASHA CORPORATION, Anguilla (AI); LIV INNOVATION SA, Lugano (CH)

( * ) Notice: Subject to any disclaimer, the term of this patent is extended or adjusted under 35 U.S.C. 154(b) by 942 days.

(21) Appl. No.: 17/432,850

(22) PCT Filed: Feb. 21, 2020

(86) PCT No.: PCT/NL2020/050112
§ 371 (c)(1),
(2) Date: Aug. 20, 2021

(87) PCT Pub. No.: WO2020/171713
PCT Pub. Date: Aug. 27, 2020

(65) Prior Publication Data
US 2022/0168235 A1    Jun. 2, 2022

(30) Foreign Application Priority Data

Feb. 21, 2019 (NL) .................................... 2022616

(51) Int. Cl.
*A61K 31/05* (2006.01)
*A61K 31/352* (2006.01)
*A61P 25/00* (2006.01)

(52) U.S. Cl.
CPC ............ *A61K 31/05* (2013.01); *A61K 31/352* (2013.01)

(58) Field of Classification Search
CPC ........ A61K 31/05; A61K 31/352; A61P 25/00
See application file for complete search history.

(56) References Cited

U.S. PATENT DOCUMENTS

| | | |
|---|---|---|
| 2017/0231948 A1 | 8/2017 | Skuratovich et al. |
| 2018/0311181 A1 | 11/2018 | Kochinke |
| 2018/0344684 A1 | 12/2018 | Vu et al. |

FOREIGN PATENT DOCUMENTS

| | | |
|---|---|---|
| CN | 107095302 | 8/2017 |
| WO | WO 2017/137992 | 8/2017 |
| WO | 2018/023163 | 2/2018 |
| WO | 2018/173049 | 9/2018 |
| WO | 2018/232448 | 12/2018 |

OTHER PUBLICATIONS

Russo EB, "Taming THC: potential cannabis synergy and phytocannabinoid-terpenoid entourage effects", Br J Pharmacol. Aug. 2011;163(7):1344-64. doi:10.1111/j.1476-5381.2011.01238.x. PMID: 21749363; PMCID: PMC3165946.
International Search Report, International Patent Application No. PCT/NL2020/050112, mailed Jun. 23, 2020, 3 pages.
Vigil, Jacob M. et al. "Effectiveness of Raw, Natural Medical Cannabis Flower for Treating Insomnia under Naturalistic Conditions" Medicines 2018, 5, 75, pp. 1-10.

*Primary Examiner* — Brenda L Coleman
(74) *Attorney, Agent, or Firm* — Casimir Jones, S.C.; Robert A. Goetz (57) ABSTRACT

The present invention relates to cannabigerol (CBG), a cannabinoid, for use in the treatment of chronic insomnia, sleeplessness and "staying in sleep" discomfort, subjective and objective sleep disorders, primary and secondary sleep disorders, insomnia related symptoms, depression, anxiety, and/or hyperactivity. The invention further relates to a pharmaceutical formulation comprising cannabinoid Cannabigerol (CBG) and cannabinoid Cannabinodiol (CBND) for use in the treatment of chronic insomnia, sleeplessness and "staying in sleep" discomfort, subjective and objective sleep disorders, primary and secondary sleep disorders, insomnia related symptoms, depression, anxiety, and/or hyperactivity, preferably wherein the ratio of CBG:CBND by weight is between 10:1 and 1:10. The invention further relates to a pharmaceutical formulation comprising cannabinoid Cannabigerol (CBG) and cannabinoid tetrahydrocannabinol (THC) for use in the treatment of chronic insomnia, sleeplessness and "staying in sleep" discomfort, subjective and objective sleep disorders, primary and secondary sleep disorders, insomnia related symptoms, depression, anxiety, and/or hyperactivity. The present invention further relates to a pharmaceutical formulation comprising cannabinoid Cannabigerol (CBG) and cannabinoid tetrahydrocannabinol (THC) for use in the treatment of depression as antidepressive and a remedy for a depressive mood, preferably wherein the ratio of CBG:THC by weight is between 10:1 and 1:10, more preferably between 1:5 and 5:1. The present invention further relates to a pharmaceutical formulation comprising cannabinoid Cannabigerol (CBG) and cannabinoid tetrahydrocannabinol (THC) for use as mood stabilizer and relaxator, preferably wherein the ratio of CBG:THC by weight is between 7:3 and 3:7, more preferably between 2:5 and 5:2.

11 Claims, 6 Drawing Sheets

CANNABIGEROL AND PHARMACEUTICAL COMPOSITIONS COMPRISING CANNABIGEROL FOR USE IN THE TREATMENT OF INSOMNIA

TECHNICAL FIELD

The present invention relates to pharmaceutical compositions comprising cannabinoid compounds and for their use in treating sleep disorders and related symptoms.

BACKGROUND

About 10% of Europe is suffering from sleep disorders ranging from restless sleep till chronic insomnia. A growing number of people are concerned about their sleep in the United states. There are an estimated 40 million, on a population of 280 million, US citizens with chronic sleep disorder (in: Insomnia: An ignored health Problem" Joan E. Hamblin M D).

All prescription drugs against disorders like insomnia and insomnia-like symptoms comprise synthetic (non-natural, non-biological) compounds and cause physical and psychological dependence when take regularly over a (prolonged) period of time, even at therapeutic doses. Withdrawal symptoms and/or effects are commonly reported. Many adverse side effects are prevalent like: restlessness, insomnia, anxiety, convulsion and death. Both physical and psychological dependence symptoms including addiction are prevalent.

The newest sleeping pills, i.e. Ambien and Sonata, are among the most widely prescribed: Ambien has two-thirds of the sleep-medication market, with sales of $1.3 billion in 2003; Sonata has sales of about $120 million. Many doctors consider these pills safer and less addictive than older medications such as Restoril. They don't have as many of the earlier drugs' side effects, such as memory problems, because they clear out of the body faster. Still, both of these drugs can last four hours or more, so they aren't the best solution for insomnia sufferers who wake up too early and can't get back to sleep.

Like Restoril and Valium, the older prescription sleep aids are benzodiazepines. Sold under the brand names Dalmane, Doral, and Halcion, they are not prescribed for sleep problems as frequently as they once were. They are long acting, so users can experience residual hangovers the next day. All (synthetic) sleep aids can be addictive, and people may experience rebound insomnia when they stop taking them. A handful of users have even suffered from amnesia, anxiety, mood swings, and hallucinations. None of the currently used treatments for insomnia is capable of fully relieving the symptoms in all cases. Patients frequently combine different treatments (medications) in an attempt to address all of their symptoms. Clearly, although numerous treatments have been developed in an attempt to control insomnia and related disorders, there is still a need in the art for effective treatments. Accordingly, the first and second aspect of the present invention is to provide such a fundamental new way of treating insomnia in a natural (biological), non-synthetic manner.

Using cannabinoid compounds (cannabinoids) as medicine, all mentioned adverse side effects will never occur, due to a complete new type of CB1 (cannabinoid receptor type 1), CB2 (cannabinoid receptor type 2) and a new G-protein coupled receptor GPR55 interaction of these cannabinoids with our natural sleep-wake cycle system. Cannabinoids counter acts this natural, body-like endo cannbinoid (anandamide-like) behaviour. The body recognized cannabinoids as "self" not foreign or alien. Even aspirin shows a LD/ED dose of 40.000 to 1 compared to cannabinoids (*Cannabis*).

Cannabinoids are exclusively found in *Cannabis sativa, ruderalis*, and indica strains and their blends. *Cannabis sativa* is the natural source of a set of at least 66 oxygen-containing aromatic hydrocarbon compounds that are known collectively as phytocannabinoids (reviewed in ElSohly, 2002). The n-propyl analogue of 9-tetrahydrocannabinol (THC) was first detected in *cannabis* by Gill et al. (1970) and named 9-tetrahydrocannabivarin (THCV) by Merkus (1971).

However, after testing 23,000 *Cannabis* drug strains on cannabinoid content, it figures that only 6 out of 66 potential cannabinoids (so called principle cannabinoids) are predominant, tetrahydrocannabinol (THC), Cannabichromene (CBC), tetrahydrocannabivarin (THCV), cannabigerol (CBG), cannabidiol (CBD) and cannabinodiol (CBND). CBD is found exclusively in the so called "Hashplant" a *C. indica* variety of a *C*. subsp Hashplant, chemotype "Hashplant".

SUMMARY

In a first aspect, the invention relates to cannabigerol (CBG), a cannabinoid, for use in the treatment of chronic insomnia, sleeplessness and "staying in sleep" discomfort, subjective and objective sleep disorders, primary and secondary sleep disorders, insomnia related symptoms, depression, anxiety, and/or hyperactivity.

In a second aspect, the invention relates to a pharmaceutical formulation comprising cannabinoid Cannabigerol (CBG) and cannabinoid Cannabinodiol (CBND) for use in the treatment of chronic insomnia, sleeplessness and "staying in sleep" discomfort, subjective and objective sleep disorders, primary and secondary sleep disorders, insomnia related symptoms, depression, anxiety, and/or hyperactivity, preferably wherein the ratio of CBG:CBND by weight is between 10:1 and 1:10.

In a third aspect, the invention relates to a pharmaceutical formulation comprising cannabinoid Cannabigerol (CBG) and cannabinoid tetrahydrocannabinol (THC) for use in the treatment of chronic insomnia, sleeplessness and "staying in sleep" discomfort, subjective and objective sleep disorders, primary and secondary sleep disorders, insomnia related symptoms, depression, anxiety, and/or hyperactivity.

In a fourth aspect, the present invention relates to, a pharmaceutical formulation comprising cannabinoid Cannabigerol (CBG) and cannabinoid tetrahydrocannabinol (THC) for use in the treatment of depression as antidepressive and a remedy for a depressive mood, preferably wherein the ratio of CBG:THC by weight is between 10:1 and 1:10, more preferably between 1:5 and 5:1.

In a fifth aspect, the present invention relates to a pharmaceutical formulation comprising cannabinoid Cannabigerol (CBG) and cannabinoid tetrahydrocannabinol (THC) for use as mood stabilizer and relaxator, preferably wherein the ratio of CBG:THC by weight is between 7:3 and 3:7, more preferably between 2:5 and 5:2.

List of Definitions

"Sleep disorder" as used in the present description means: a medical disorder of the sleep patterns of a person.

"Chronic sleep disorder" as used in the present description means: a sleep disorder that occurs for a longer period of time.

"Primary sleep disorder" as used in the present description means: a sleep disorder not attributable to another medical or psychological condition.

"Secondary sleep disorder" as used in the present description means: a sleep disorder attributable to another medical problem, such as depression, thyroid problems, stroke, arthritis, or asthma.

"Subjective sleep disorder" as used in the present description means: a sleep disorder that is based on someone's opinion (e.g. physical complaints), which can differ between two persons.

"Objective sleep disorder" as used in the present description means: a sleep disorder that is indicated with facts that can be proved easily (e.g. measured data).

"Self-titration" as used in the present description means: to adjust the dosage of your own medication as needed.

"Chemotype" as used in the present description means: a chemically distinct entity in a plant or microorganism, with differences in the composition of the secondary metabolites. A chemotype is sometimes called a chemovar. Secondary metabolites are organic compounds produced by bacteria, fungi, or plants which are not directly involved in the normal growth, development, or reproduction of the organism.

"TLC" as used in the present description stands for thin-layer chromatography. This is a chromatography technique used to separate non-volatile mixtures. Thin-layer chromatography is performed on a sheet of glass, plastic, or aluminium foil, which is coated with a thin layer of adsorbent material, usually silica gel, aluminium oxide (alumina), or cellulose. This layer of adsorbent is known as the stationary phase. After the sample has been applied on the plate, a solvent or solvent mixture (known as the mobile phase) is drawn up the plate via capillary action. Because different analytes ascend the TLC plate at different rates, separation is achieved.

"*Flos*" as used in the present description means: the dried flower tips of a particular *Cannabis* strain, plant, variety or chemovar.

BRIEF DESCRIPTION OF THE DRAWINGS

The present invention is described hereinafter with reference to the accompanying drawings in which embodiments of the present invention are shown and in which like reference numbers indicate the same or similar elements.

FIG. 3 shows that the probability that a rat wakes up is significantly less in the light period compared with the dark period. The probability that *cannabis* treated rats stop sleeping is significantly less compared with placebo-oil treated animals.

FIG. 4 shows that *cannabis* treated rats have significantly less power in EEG of active and passive behavior compared to oil treated rats and baseline conditions. Oil treated rats have less power in active behavior EEG compared with baseline, but more power compared with *cannabis* treated rats. The sedative or hypnotic activity was determined by observing the action of the compounds on the EEG of curarized rats and also on the wake-sleep states in freely moving, implanted rats and cats. In curarized rats, the products to be studied were injected intraperitoneally or orally at doses increasing from 0.1 to 30 mg/kg. They induce sleep traces starting from doses ranging from 0.1 to 10 mg/kg, administered intraperitoneally or orally. In freely moving, implanted rats, the products to be studied were injected intraperitoneally or orally at a single dose ranging from 1 to 10 mg/kg. At these doses, they reduce the total wake time by 13 to 44%, without significantly changing the total paradoxical sleep time, certain products even increasing the total duration of this phase of sleep. The results of these various tests show that the compounds of the invention possess anxiolytic, anti-anoxic, sleep-inducing, hypnotic and anticonvulsant properties

DESCRIPTION OF THE INVENTION

In an aspect, the invention relates to cannabigerol (CBG), a cannabinoid, for use in the treatment of chronic insomnia. In an aspect, the invention relates to cannabigerol (CBG), a cannabinoid, for use in the treatment of sleeplessness and "staying in sleep" discomfort or for use in improving subjective and objective sleep disorders, primary and secondary sleep disorders. In an aspect, the invention relates to pharmaceutical formulation comprising cannabinoid Cannabigerol (CBG) and cannabinoid Cannabinodiol (CBND) for use in the treatment of chronic insomnia wherein the ratio of CBG:CBND by weight is between 10:1 and 1:10. In an aspect, the invention relates to a pharmaceutical formulation comprising cannabinoid Cannabigerol (CBG) and cannabinoid Cannabidiol (CBD) for use in the treatment of insomnia and insomnia related symptoms and depression. In an aspect, the invention relates to a pharmaceutical formulation comprising cannabinoid Cannabigerol (CBG) and cannabinoid Cannabinodiol (CBND) and cannabinoid tetrahydrocannabinol (THC) for use in the treatment of insomnia, anxiety, anti-depressive, hyperactivity and insomnia related symptoms, preferably wherein the weight ratio of CBG:CBND:THC is between 10-1:1-5:1-5 or between 1-10:5-1:5-1. In an aspect, the invention relates to *Cannabis simplex* comprising in weight percentages 4-10% of cannabinoid THC, 3-10% of cannabinoid CBG and 3-10% of cannabinoid CBND for use in the treatment of insomnia, anxiety, anti-depressive, hyperactivity and insomnia related symptoms. In an aspect, the invention relates to a pharmaceutical formulation comprising cannabinoid Cannabigerol (CBG) and cannabinoid Cannabinodiol (CBND) and cannabinoid cannabichromene (CBC) for use in the treatment of insomnia, anxiety, hyperactivity, anti-depressive and insomnia related symptoms. In an aspect, the invention relates to a pharmaceutical formulation comprising cannabinoid Cannabigerol (CBG) and cannabinoid tetrahydrocannabinol (THC) for use in the treatment of depression as anti-depressive and a remedy for a depressive mood, wherein the ratio of CBG:THC by weight is between 10:1 and 1:10, preferably between 1:5 and 5:1. In an aspect, the invention relates to a pharmaceutical formulation comprising cannabinoid Cannabigerol (CBG) and cannabinoid tetrahydrocannabinol (THC) for use as mood stabilizer and relaxator, wherein the ratio of CBG:THC by weight is between 7:3 and 3:7, preferably between 2:5 and 5:2. In an aspect, the invention relates to a Cannabigerol or pharmaceutical formulation, wherein the cannabinoids are packaged for deliv- ery in a titratable dosage form. In an aspect, the invention relates to a Cannabigerol or pharmaceutical formulation, wherein a unit dose comprises in the range of 2-12 mg, preferably between 7-8.5 mg, of each cannabinoid present. In an aspect, the invention relates to a pharmaceutical formulation, wherein CBG is administered separately, simultaneously or sequentially to CBND or CBC or THC. In an aspect, the invention relates to a pharmaceutical formulation, wherein the maximum daily dosage of CBG is less than or equal to 120 mg. In an aspect, the invention relates to a pharmaceutical formulation, wherein the maximum daily dosage of cannabinoids is less than or equal to 130 mg of CBND, less than or equal to 20-80 mg of THC and less than or equal to 130 mg of CBC. In an aspect, the invention relates to a Cannabigerol or pharmaceutical formulation, wherein the cannabinoid(s) is/are packaged for delivery such that delivery is targeted to an area selected from the group consisting of: sublingual, buccal, oral, rectal, nasal and the pulmonary system. In an aspect, the invention relates to a Cannabigerol or pharmaceutical formulation, wherein the cannabinoid(s) is/are in the form selected from the group consisting of: gel, gel spray, tablet, liquid, capsule, for vaporization and for nebulisation. In an aspect, the invention relates to a Cannabigerol or pharmaceutical formulation, wherein the cannabinoid(s) is/are synthetic. In an aspect, the invention relates to a Cannabigerol or pharmaceutical formulation, wherein the cannabinoid(s) is/are for administration in combination with one or more other drugs, preferably one or more synthetic sedatives or sleeping pills.

In an embodiment, the pharmaceutical formulation for use comprising CBG and CBND, further comprising cannabinoid tetrahydrocannabinol (THC), preferably wherein the weight ratio of CBG:CBND:THC is between 10-1:1-5:1-5 or between 1-10:5-1:5-1. In an embodiment, the pharmaceutical formulation for use comprising CBG and optionally CBND, and optionally THC, further comprising cannabinoid cannabichromene (CBC). In an embodiment of said pharmaceutical composition for use, said CBG is administered separately, simultaneously or sequentially to said CBND and/or CBC and/or THC. In an embodiment of the CBG or pharmaceutical composition for use, wherein the maximum daily dosage of CBG is less than or equal to 120 mg. In an embodiment of said pharmaceutical composition for use, the maximum daily dosage of cannabinoids is less than or equal to 130 mg of CBND, less than or equal to 20-80 mg of THC and less than or equal to 130 mg of CBC.

In an embodiment of said CBG or pharmaceutical composition for use, the one or more cannabinoids are packaged for delivery such that delivery is targeted to an area selected from the group consisting of: sublingual, buccal, oral, rectal, nasal and the pulmonary system. In an embodiment of said CBG or pharmaceutical composition for use, the one or more cannabinoids are in the form selected from the group consisting of: gel, gel spray, tablet, liquid, capsule, for vaporization and for nebulisation. In an embodiment of said CBG or pharmaceutical composition for use, the one or more cannabinoids are synthetic. In an embodiment of said CBG or pharmaceutical composition for use, the one or more cannabinoids are for administration in combination with one or more other drugs, preferably one or more synthetic sedatives or sleeping pills.

The present invention further relates to pharmaceutical compositions of cannabigerol (CBG), cannabichromene (CBC), cannabinol (CBN) and cannabinodiol (CBND) for the treatment of sleep disorders, primary and secondary sleep disorders, excessive somnolence, insomnia and other insomnia related symptoms, as anti-depressive, use as sedative and a remedy against anxiety.

Cannabigerol (CBG-C5) was the first compound isolated from the resin of marijuana as a pure chemical substance (Gaoni and Mechoulam, 1964a). Although CBG-type compounds are inactive when compared to Δ9-THC (Grunfeld and Edery, 1969 and Mechoulam et al., 1970), they show considerable antibacterial activity against gram positive bacteria (Mechoulam and Gaoni, 1965). There are currently seven CBG-type compounds known. The most recently isolated compound, cannabinerolic acid, is the trans-isomer of cannabigerolic acid (Taura et al., 1995). All other CBG-type compounds have cis-geometry. Independent claims are also included for the compounds listed in table 1.

Cannabigerol
CBG type cannabinoids

TABLE 1

| CBG type cannabinoids | | | | | | |
|---|---|---|---|---|---|---|
| Compound | cls/trans | $R^1$ | $R^2$ | $R^3$ | $R^4$ | $R^5$ |
| Cannabigerolic acid A [(E)-CBGA-C$_5$ A] | cls | COOH | n-C$_5$H$_{11}$ | H | (CH$_2$)$_2$CH=C(CH$_3$)$_2$ | Me |
| Cannabigerolic acid A monomethyl ether [(E)-CBGAM-C$_5$ A] | cls | COOH | n-C$_5$H$_{11}$ | Me | (CH$_2$)$_2$CH=C(CH$_3$)$_2$ | Me |
| Cannabigerol [(E)-CBG-C$_5$ A] | cls | H | n-C$_5$H$_{11}$ | H | (CH$_2$)$_2$CH=C(CH$_3$)$_2$ | Me |
| Cannabigerol momoethyl ether [(E)-CBGM-C$_5$] | cls | H | n-C$_5$H$_{11}$ | Me | (CH$_2$)$_2$CH=C(CH$_3$)$_2$ | Me |
| Cannabigerovarinic acid A | cls | COOH | n-C$_3$H$_7$ | H | (CH$_2$)$_2$CH=C(CH$_3$)$_2$ | Me |

TABLE 1-continued

| CBG type cannabinoids | | | | | | |
|---|---|---|---|---|---|---|
| Compound | cis/trans | R¹ | R² | R³ | R⁴ | R⁵ |
| [(E)-CBGVA-C₃ A] Cannabigerovarin [(E)-CBGV-C₃] | cis | H | n-C₃H₇ | H | (CH₂)₂CH=C(CH₃)₂ | Me |
| Cannabigerolic acid A [(Z)-CBGA-C₆ A] | trans | COOH | n-C₅H₁₁ | H | Me | (CH₂)₂CH=C(CH₃)₂ | compositions comprising a therapeutically effective amount of the cannabinoid cannabigerol (OBO) for the preparation of a new pharmaceutical composition for the treatment of sleep disorders, primary and secondary sleep disorders, excessive somnolence, insomnia and other insomnia related symptoms, as anti-depressive, use as sedative and a remedy against anxiety.

Cannabigerol

In particular, the present invention further relates to the use of pharmaceutical compositions comprising therapeutically effective amount of the cannabinoids cannabigerol (CBG) and cannabinodiol (CBND) for the preparation of a new pharmaceutical composition for the treatment of sleep disorders, primary and secondary sleep disorders, excessive somnolence, insomnia and other insomnia related symptoms, as anti-depressive, use as sedative and a remedy against anxiety.

CBND type cannabinoids have the following structure:

In cannabinodiol CBND-C₅ R¹ is C₅H₁₁. CBND type cannabinoids includes formulas wherein R¹ is CH₃, C₂H₅, C₃H₇ or C₄H₉.

Cannabinodivarin CBNDV, also known as, CBND-C₃ has R¹=n-C₃H₇.

CBND-C5

CBND-C3

The present invention further relates to the use of pharmaceutical compositions comprising therapeutically effective amounts of the cannabinoid compounds (cannabinoids) cannabinodiol (CBND) and cannabigerol (CBG) for the preparation of new poly-pharmaceutical compositions for the treatment of sleep disorders, primary and secondary sleep disorders, excessive somnolence, insomnia and other insomnia related symptoms, as anti-depressive, use as sedative and a remedy against anxiety.

The present invention further relates to the use of a combination of two or more cannabinoids for the treatment of (chronic) insomnia (primary and secondary) and improving subjective and objective sleep disorders. In addition, these cannabinoids are for use against trouble falling asleep or staying asleep. In addition, these cannabinoids are for use as a sedative, for depressive disorders (antidepressive) and treatment of stress related symptoms. Additionally, these cannabinoids are used as mood stabilizers and against hyperactivity. Preferably, cannabigerol (CBG) and its acid analogue CBGA (CBG-acid) are used. More preferred is the cannabinoid combination cannabigerol (CBG), and cannabinodiol (CBND) and the sedative acting cannabinoid cannabidiol (CBD). For other insomnia related symptoms a preferred combination is the combination of Δ9-Tetrahydrocannabinol (THC) (relative low concentration), cannabigerol (CBG), cannabidiol (CBD), and cannabinodiol (CBND). More preferably, the cannabinoids are in a predefined ratio by weight of approximately 1:5-10:5-10:5-10-1-10 for THC, CBG, CBD and CBND respectively. CBC; 5-10. In other words, the cannabinoids are in a predefined ratio by weight of approximately 1 part by weight of THC to 5-10 parts by weight of CBG to 5-10 parts by weight of CBD to 5-10 or 1-10 parts by weight of CBND and optionally 5-10 parts by weight of CBC. In an aspect, the invention relates to a pharmaceutical composition comprising cannabigerol (CBG) and Cannabinodiol (CBND) and tetrahydrocannabinol (THC) for use in the treatment of insomnia and insomnia related symptoms. In an aspect, the invention relates to a pharmaceutical composition comprising Cannabigerol (CBG), Cannabinodiol (CBND) and cannabichromene (CBC) for use in the treatment of insomnia. In an aspect, the invention relates to a pharmaceutical composition comprising Cannabigerol (CBG), Cannabinodiol (CBND), cannabichromene (CBC) and tetrahydrocannabinol (THC) for use in the treatment of insomnia, anxiety, hyperactivity, as anti-depressive and insomnia related symptoms.

Δ9-Tetrahydrocannabinol (THC)

The present invention is directed to the use of cannabinoids, preferably cannabigerol (CBG), as natural agent. Conclusively, cannabinoids act "self" in body and mind, in contrast to all synthetic medicines which will be recognized in the body as "non-self", or foreign. Only when the latter is the case, side effects are to be expected.

Cannabinoids are from pharmaceutical and toxicological point of view the safest group of drugs, and show the longest long-term safety history of at least 4,000 years as well the longest scientific life cycle of any other drug.

Over the past 50 years, a considerable research in medicinal chemistry has been carried out around the natural constituents of *Cannabis sativa* L. Following the identification of Δ9-Tetrahydrocannabinol (Δ9-THC) in 1964, critical chemical modifications, e.g. variation of the side chain at C(3) and the opening of the tricyclic scaffold, have led to the characterization of potent and cannabinoid receptor subtype-selective ligands. Those ligands that demonstrate high affinity for the cannabinoid receptors and good biological efficacy are still used as powerful pharmacological tools.

This review summarizes past as well as recent developments in the structure-activity relationships of phytocannabinoids. In recent years, ICRS researchers have determined that cannabinoids modulate the activity of virtually every messenger system in the brain, like GABA, dopamine, acetylcholine, endorphins, prolactin, glutamate, serotonin. This may explain why *Cannabis* has an impact on so many medical conditions. (J. of the California *Cannabis* Research Medical Group, summer 2003).

The subject of the present invention is the use of pharmaceutical compositions of CBG and THC, and optionally, CBND, CBD and CBC as strong sleep promoting polypharmaceutical cannabinoid formulations with different combinations for different applications like insomnia, depression and hyperactivity ("lite" version) applications and other insomnia like symptoms. For use according to the present invention, CBG may be combined with another cannabinoid-based active ingredient chosen from one of the following suspected bioactive compounds (named "cryptic" spots on the TLC plate of the Cannalytics method described below):

1—plastids (xanthophylls-like);
2—plant pigments chlorophylle a and b, xanthophylls and phaeophytin;
3—components of the plastids such as membranes (thylakolid) and proteins;
4—the cannabinoids cannabinodiol (CBND) and cannabidiol (CBD).

Alpha nova Diagnostics tested more than 45,000 *Cannabis sativa*, indica, and *ruderalis* strains and their blends with the recently developed CannalyticsR method, a TLC based cannabinoid separation method that separates all the neutral and the acidic cannabinoids on a small TLC plate. The cannabinoids THC, THV, CBG, CBD, CBN, CBND, CBC, CBGM and their acid analogues are all visible as discrete colored spots on this plate.

The method is a cheap, rapid and cost-efficient way for high throughput screenings of many accessions.

This method allowed deduction, and therefore, for the first time, the introduction of a new chemotaxonomic classification system merely based on the cannabinoid composition of the plant samples (strains). 15 chemotypes are defined and many more sub-chemotypes are lately added. The samples given to panel members (accessions) contained *Cannabis flos*, the dried flower tips of the female *Cannabis* plant. Panel-mediated testing and anecdotic evidence from recreational users from the Netherlands and Spain revealed even so characteristic cannabinoid profile-effect relationships. All the 45,000 different "strains" were collected and compared to the panel data and data derived from retrospective (meta-) research and anecdotal evidence mainly originated from users, for both recreative and medicinal usage, from the Netherlands. Accession from Spain is included as a parameter and seemed important for the chemotaxonomic scheme for *Cannabis* species.

The anecdotal evidence is derived from and the panel members are selected from persons, men and women, of the age of 18 till 72 years old. They consumed *cannabis* joints or vapor having defined cannabinoid profiles, and record the effect during time. Monitoring takes 24 hours, to include data about wear-off problems after night (the next day). The cannabinoids according to the invention may for example be consumed as follows:

1—Administered as *Cannabis simplex* per 50 mg unit dose for self-titration. Administered as powder in a tea potion based manner or, preferably as vapor.
2—Administered as *Cannabis simplex* trichome extract 5 mg unit dose for self-titration.
3—Administered as isolated corresponding cannabinoid oils in titratable formulation in capsules with a unit dose of 2 mg each corresponding cannabinoid oils of CBG, CBND and CBC.

Self-administration is a key feature, actually for all medicines, and this is possible with the present invention, especially for *Cannabis* related medicines. Single-blind, a select randomized 50 mg *Cannabis simplex* medical grade dosages, administered as vapor or tobacco joints with 50 mg *Cannabis simplex*.

All panel members used a 50 mg *Cannabis simplex* samples as vapor or joints, from medical grade quality. Administration: Ad libitum. They had to stop when the beneficial effects were pronounced enough. The time span of this experiment was 2 years.

Figure 1A:
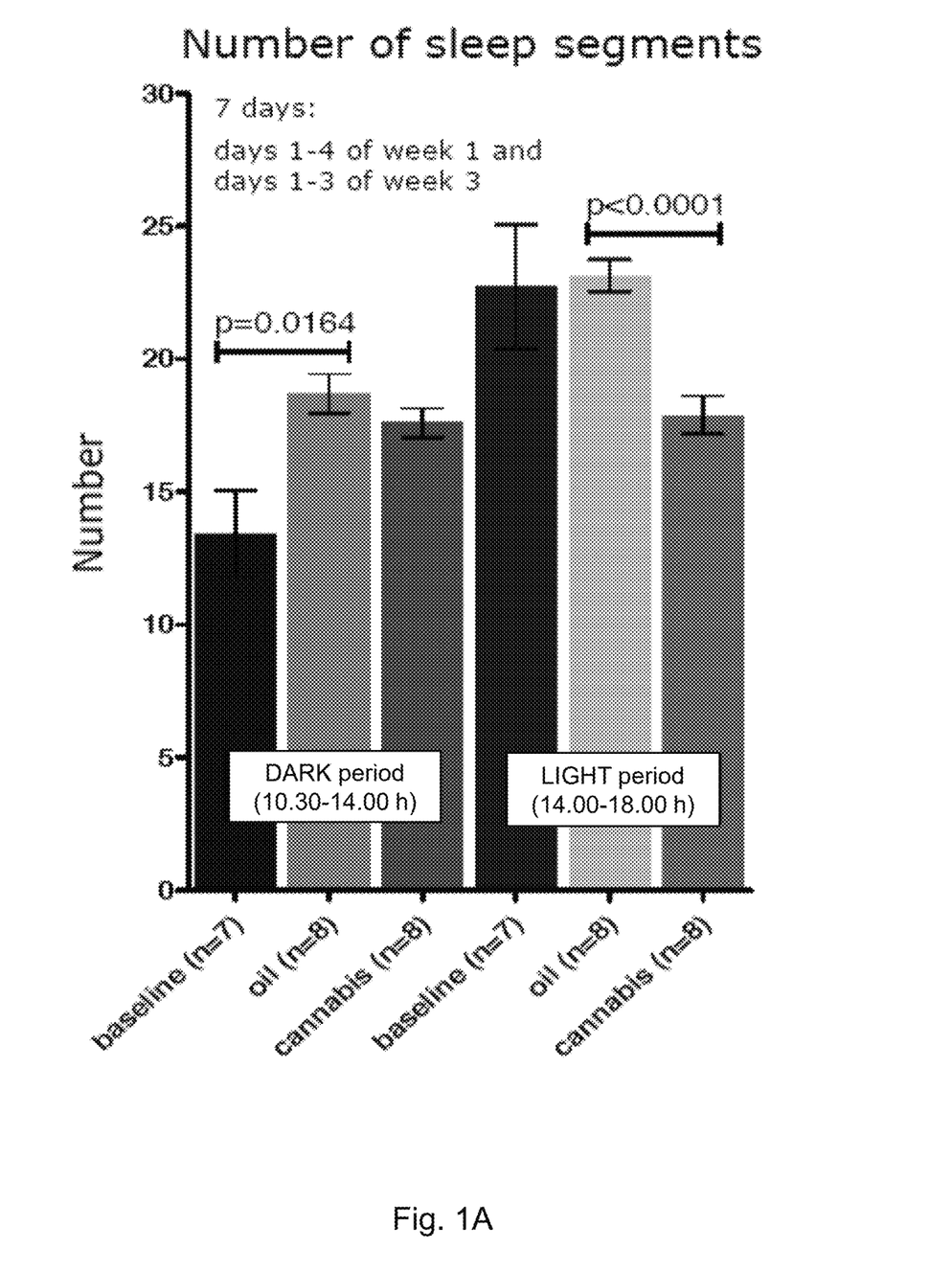
FIG. 1a shows the number of sleep segments.
Figure 1B:
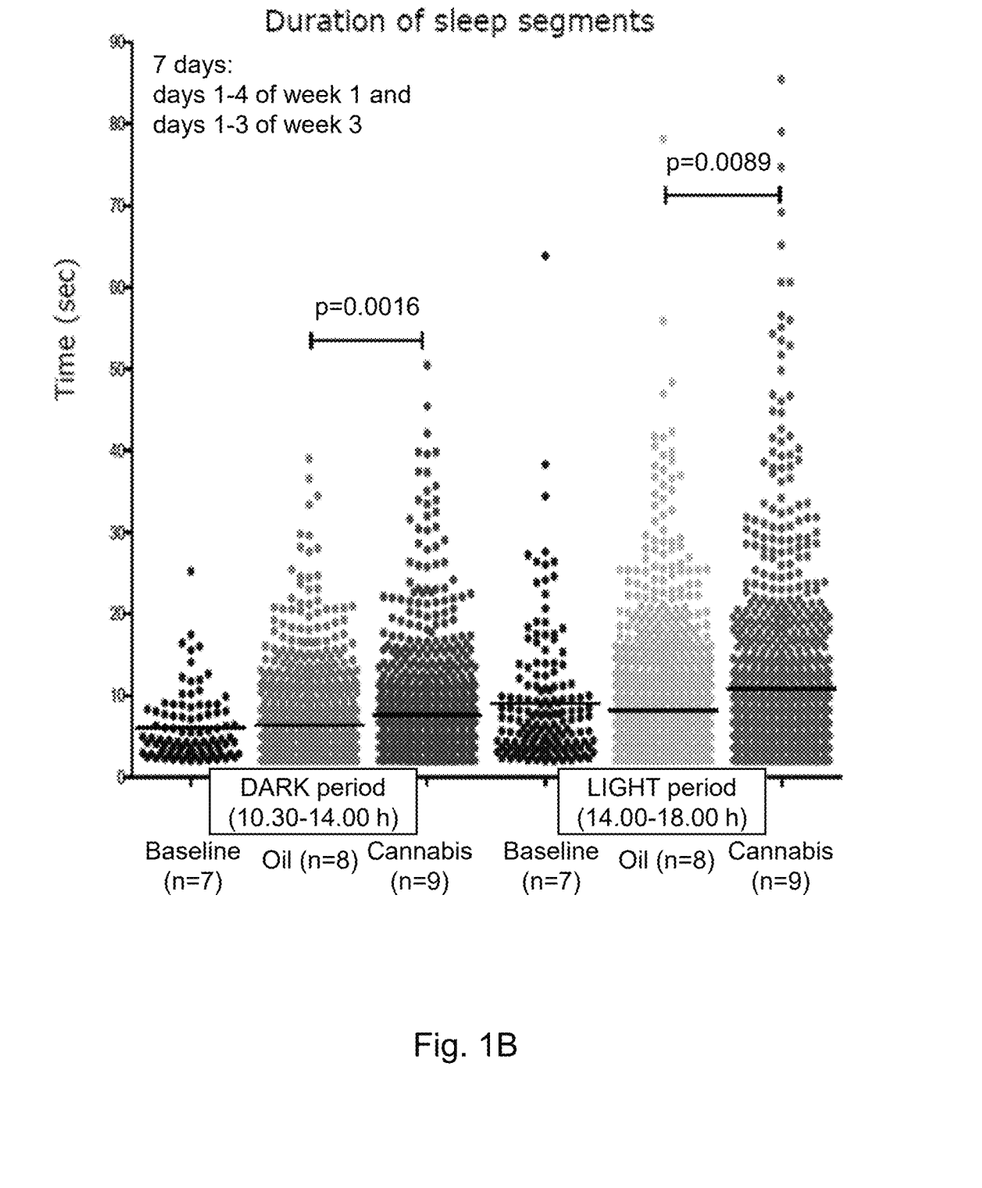
FIG. 1b shows the duration of sleep segments.
Figure 2:
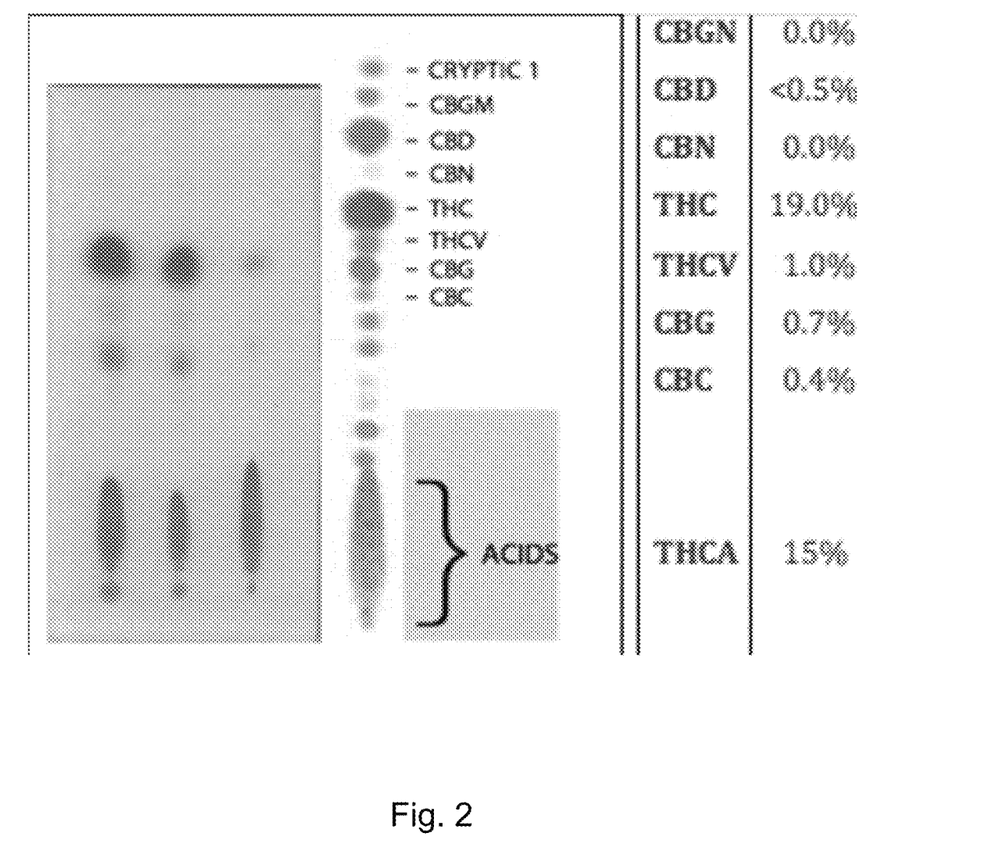
FIG. 2 shows an TLC cannabinoid profile of a strong sedative and antidepressant. This indicates the cannabinoid composition responsible for the sleep inducing effect of the strain AK50.
Figure 3:
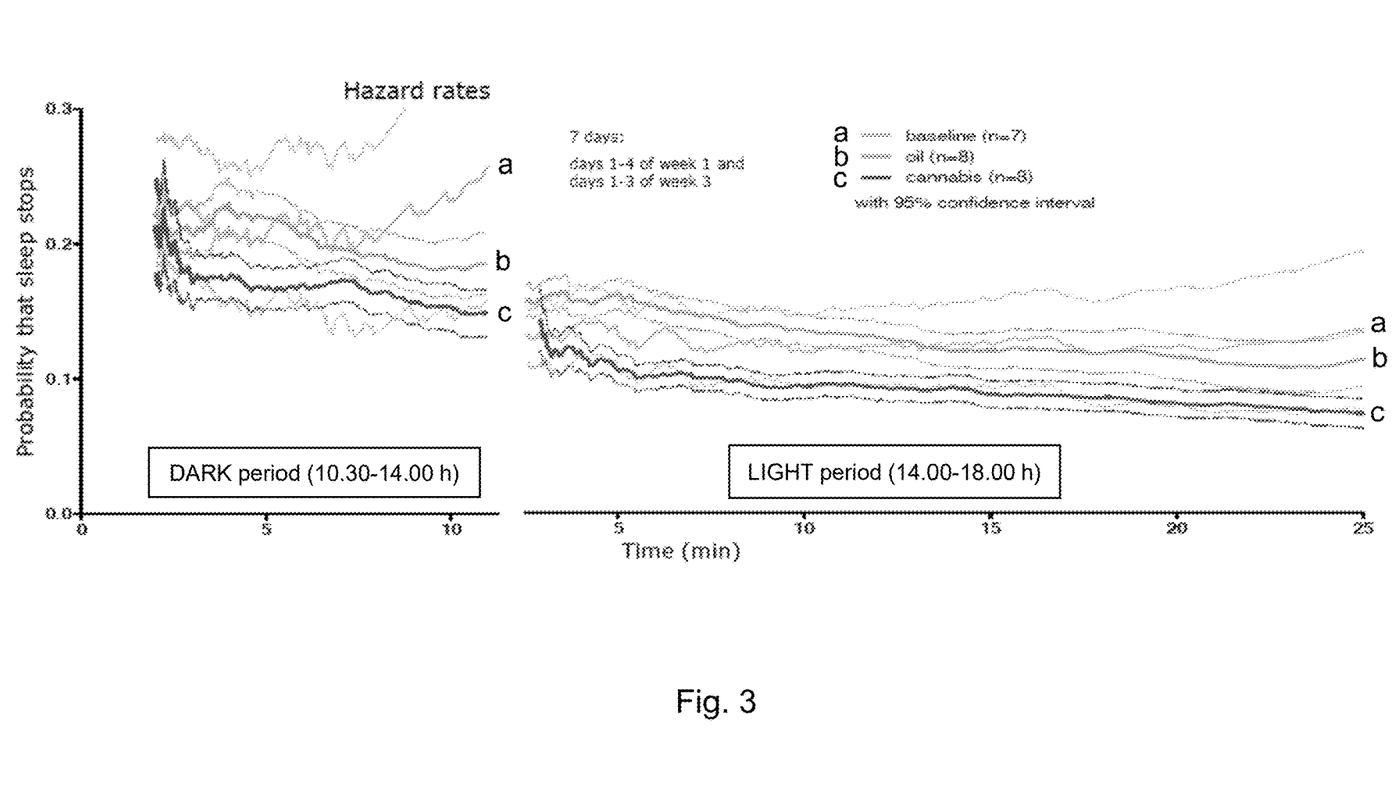
FIG. 3 shows hazard rates. The hazard function quantifies changes in the probability that an event (stop sleeping/waking up) occurs in some small time interval given that it has not occurred yet.
Figure 4:
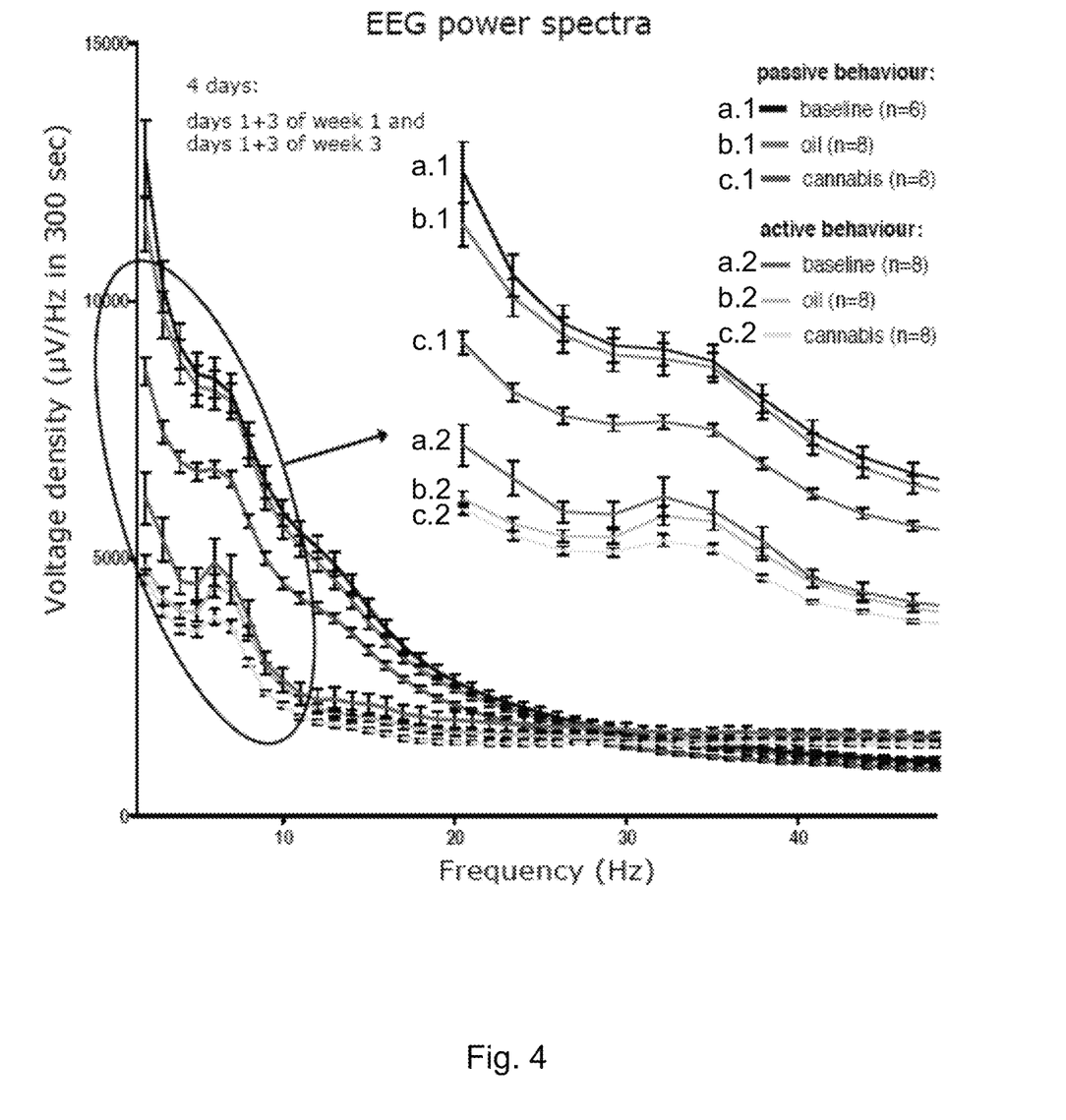
FIG. 4 shows EEG power spectra.
Figure 5:
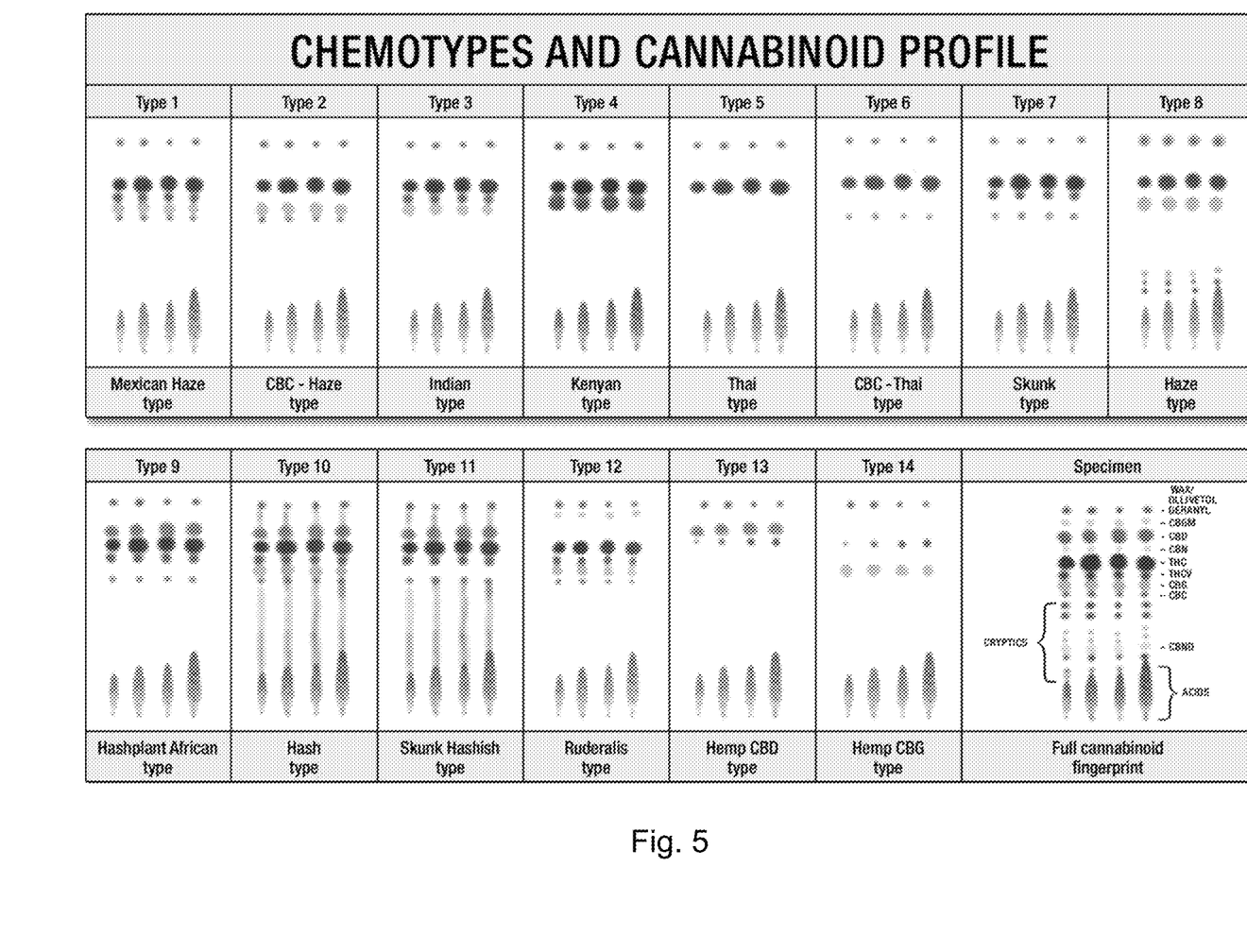
FIG. 5 shows the chemotypes and their cannabinoid profiles.

Specific *Cannabis simplex* accessions from the Netherlands and purchased at local coffee-shops spread over the country were used for the panels, with trivial names and well known cannabinoid profile and effect (anecdotic) relationships were used:

See FIG. 5: A new taxonomic chemotype chart for *Cannabis*

Data are derived from the above described 'long term' panel research and anecdotic confirmation by all the stakeholders: breeders (prospectus), coffeeshop holders and users are as follows. Three formulations A, B and C (table 2) were used in the panel session; trichome fraction (crystal) powder with a unit dose of 0.1 mg, 2 mg and 12 mg, respectively, and pure cannabinoid oils with a unit dose of 2-20 mg and *Cannabis simplex* with a unit dose of 50 mg. Three delivery systems were used; vapor, joints and tea potion based, with a unit dosage of Formulations A, B and C:

Formulation A: "White widow" chemotype 1 subtype: "WW" Comprising THC, CBG and CBC effect: "indica", "stoned", "drowsiness", sleep, strong sleep;

Formulation B: "Power plant" chemotype 1 subtype: "PP" effect: "*Sativa*"; activating, energizing, anti-sleep;

Formulation C: "Nepal" chemotype 7 subtype 1 effect: suppressing appetite and food intake.

TABLE 2

Formulations used in the test.

| Formulation | Name | Chemotype | Subtype | Effects |
| --- | --- | --- | --- | --- |
| Formulation A | "White widow" | 1 | "WW" | Indica, stoned, drowsiness, sleep, strong sleep |
| Formulation B | "Power plant" | 1 | "PP" | Sativa, activating, energizing, anti-sleep |
| Formulation C | "Nepal" | 7 | 1 | Suppressing appetite and food intake |

The effects are dosage and patient related. An object of the present invention is the use of the cannabinoids of these specific chemotypes which are responsible for these particularly effects such as suppressing appetite, sleep and activating formulations (corresponding patent applications pending) for the preparation of medicaments useful in the prevention of sleep anomalies, insomnia related disorders, depressive, anxiety and hyperactivity (CBG and THC formulation). Personal differences in doses-effect relationships are recorded and are in agreement with the individual genetically determined differences in the potential of the body to break down foreign compounds by biotransformation and elimination routes cq. the cytochrome P450 broad working frame, enzyme family concerning the breakdown of all foreign compounds in the body even cannabinoids are under attack. The personal differences are genetically determined even so the number of receptors for (all) neurotransmittors (GABA, seretonine, acethylcholine, DOPA, noradrenaline) which counter act with anandamide, so with cannabinoids.

All the tested specific chemotypes surprisingly revealed strains with a strong sleep provoking effect on 100% of the panel (N=67) members records. Comparison to the cannabinoid profile revealed the cannabinoids responsible for this effect.

All subjects attained good or very good deep (in high concentration range) "narcotic" sleep caused by the present invention, cannabigerol (CBG) as sleep inducing agent.

In the same way some strains show on all panel members (N=67) an effect of strong appetite loss, due to a natural cannabinoid based THC antagonist (patent application pending).

In the same way some strains show even more on all panel (N=67) members, surprisingly an energizing, activating body and mind effect, quit opposite to the "sleep" cannabinoid profile (patent application pending). Varieties with the trivial name "Power plant" will show this effect on panel members (patent application pending).

The present invention describes the sleeping properties of cannabigerol (CBG) and cannabinodiol (CBND).

Because of the fact that cannabinoids mimic the effect of our natural endocanabinoid system, no severe side effects are to be expected and no overdose makes this so (it is not shown that a deadly overdose is possible), and indeed no "death" reports are recorded at least until 2018.

From a pharmaceutical and toxicological point of view, cannabinoids are the safest drugs that ever existed.

Cannabinoids have a long historical and scientific life cycle.

Cannabinoids, in contrast to all other synthetic sedatives, are the only medicinal drugs in the commercial circuit that have a very long-term safety.

Cannabinoids are from a pharmaceutical point of view, a group of harmless drugs, especially compared to synthetic artificial pharmaca like barbiturates, benzodiazepines, imidazopyridines and many other types of sedatives They all lack long term trials.

The only way to assure public safety is to do long-term randomizing trials, to avoid debacles after introduction of drugs like VioxxR and recently RimonabantR (not approved for the US market) and in fact these drugs are inverse agonists towards CB1 receptors.

Therefore is it reasonable to omit stage 1 and the stage 2 trials for *Cannabis* research. Anecdotal evidence has emerged that suggests that patients with a range of conditions and diseases can obtain significant symptom relief from illicit or "street" *Cannabis* or *Cannabis* from the coffeeshops in the Netherlands.

Subsequently, interest has grown and research has been conducted into the therapeutic uses of cannabinoids. This research was part of a coordinated program and involved small trials.

In the Netherlands the liberated research into the cannabinoid chemistry and free possession of *Cannabis* makes it possible to gain tremendous information about all aspects concerning *Cannabis*, her cannabinoid profile and effect relationships.

Cannabigerol alone and the formulation of cannabigerol (CBG) and cannabinodiol (CBND) provokes the well-recorded "indica" or "stoned" effects; drowsiness and in a doses and patient related manner, sleepy. Low THC strains with concomitant high CBG, makes the strain according to panel data, "narcotic". The presence of THC causes activation of the sleep-inducing properties of CBG, hence there is a synergy between THC and CBG. When CBND is added, it functions as catalyst and enhances the effect of THC with CBG. Furthermore, by combining CBND with CBG the sleep-inducing properties of CBG are enhanced, i.e. there is a synergy between CBND and CBG. The combination of THC, CBG and CBND is the most effective.

Preferred features of the invention will now be described in further detail. Features described as being preferred in relation to one aspect of the invention apply mutatis mutandis to all other aspects, unless clearly stated otherwise.

Preferably the use of the cannabinoids in the manufacture of a pharmaceutical formulation are for use in the treatment of chronic insomnia.

Preferably the use of cannabinoids in the manufacture of a pharmaceutical formulation are for use in the treatment of sleeplessness and "staying in sleep" discomfort.

Preferably the use of cannabinoids in the manufacture of a pharmaceutical formulation with CBG and THC only are for use in the treatment of depression as anti-depressive and a remedy for a depressive mood wherein the ratio of CBG:THC by weight is between 10:1 and 1:10, preferably between 1:5 and 5:1.

Preferably the use of cannabinoids in the manufacture of a pharmaceutical formulation are for use in the treatment of improving subjective and objective sleep disorders.

Preferably the use of cannabinoids in the manufacture of a pharmaceutical formulation are for use in the treatment of against hyperactivity.

Preferably the use of cannabinoids in the manufacture of a pharmaceutical formulation are for use as mood stabilizer and for relaxation wherein the ratio of CBG and CBND by weight is between 7:3 and 3:7, preferably between 2:5 and 5:2.

Favorable the cannabinoids are packaged for delivery in a titratable dosage form. Preferably the cannabinoid CBG is administrated separately, simultaneously or sequentially to the cannabinoids CBND and/or THC formulations.

The administration of a combination of cannabinoids such as CBG, CBND and CBD to a patient could either be at the same time, wherein the cannabinoids would be contained in the same formulation. The cannabinoids could also be administered together or at separate times for example; a formulation containing CBG could be administered to a patient at a fixed time prior to a formulation containing CBND and/or CBD and/or THC in order to ameliorate some of the "narcotic" side effects of the cannabinoid cocktail.

The cannabinoids could also be administered consecutively to a patient if required.

In the preparation of the pharmaceuticals, a solvent (e.g., water or physiological saline), solubilizing agent (e.g., ethanol, Polysorbates, or Cremophor EL7), agent for making isotonicity, preservative, antioxidizing agent, excipient (e.g., lactose, starch, crystalline cellulose, mannitol, maltose, calcium hydrogen phosphate, light silicic acid anhydride, or calcium carbonate), binder (e.g., starch, polivinylpyrrolidone, hydroxypropyl cellulose, ethyl cellulose, carboxy methyl cellulose, or gum Arabic), lubricant (e.g., magnesium stearate, talc or hardened oils), or stabilizer (e.g. lactose, mannitol, maltose, polysorbates, macrogols, or polyoxyethylene hardened castor oils) can be added. If necessary, glycerin, dimethylacetarnide, 70% sodium lactate, a surfactant, or a basic substance such as sodium hydroxide, ethylenediamine, ethanolamine, sodium bicarbonate, arginine, meglumine, or trisaminomethane is added. Pharmaceutical preparations such as solutions, tablets granules or capsules can be formed with these components. Compositions for slow release of the compound can be formed as described in U.S. Pat. No. 4,880,830.

Additionally the pharmaceutical formulation may further comprise one or more carriers or excipients selected from the group consisting of diluent, solvent, absorbent, antiadherent, binder, coatings, disintegrant, surfactant, dissolving agent, solubilizing agent, bioadhesive agent, polysaccharides, polymers, copolymers, fast dissolving tablet (FDT) type excipient, bioavailability enhancing agent, Thin Film type excipient, PharmFilm type excipient, mucoadhesive type excipient, acidifying agents, probiotic agents, protective agents, antioxidants, effervescent excipient, dispersing agents, glidant, flavours, colours, sweetener, thickener, lubricant, sorbents, preservatives, and any combination thereof. Preferably the carrier solvents are ethanol and/or propylene glycol. More preferably the ratio of ethanol to propylene and glycol is between 4:1 and 1:4. More preferably still the ratio is substantially 1:1. It is further within the scope to provide the composition as defined in any of the above, wherein the solvent is ethanol.

Generally, the oral administration methods and formulations of the present invention provide between about 11 mg and about 200 mg, for example between about 10 mg and about 100 mg per day, or between about 20 mg and about 60 mg per day, administered about 1, 2, 3, 4 or 5 times daily of one of the formulations with defined weight ratios of the cannabinoids cannabigerol (CBG) and cannabinodiol (CBND) and THC, wherein the ratio of CBG:CBND:THC by weight is between 10-1:1-5:1-5 or: 1-10:5-1:5-1 respectively. More preferably the ratio for *Cannabis simplex* is 4-10% THC and 3-10% of CBG and 3-10% of CBND (strong formulation; CBG:CBND:THC of 3-10:10-3:4-1. (i.e. excluding excipients, carriers, and any of the optional additional active ingredients described herein). If desired, the daily dose may include two or more unit doses, i.e., tablets, cachets or capsules, to be administered each day.

Additionally, CBD will be administered if necessary, together with all the formulations depicted above. This formulation might be depicted as "a strong working" formulation. The invention is further defined by reference to one embodiment, in which the cannabinoid composition of *Cannabis simplex* is changed by a curing procedure described below, in order to increase the CBD content from 0% to 40% of the total trichomic oil content.

More preferably the cannabinoid(s) are in the form selected from one or more of the following: gel, spray, tablet, liquid; e.g. tea potion based, capsule, for vaporization and for nebulisation.

The term "titrate" is defined as meaning that the patient is provided with a medication that is in such a form that smaller doses than the unit dose (50 mg *Cannabis simplex* and 5 mg for the oil and trichom-fraction formulations) can be taken.

A "unit dose" is herein defined as a maximum dose of medication that can be taken at any time or within a specified dosage period such as 3 hours when THC is present or 6 hours when CBG and CBC predominates in the formulation.

Titration of doses in a patient related manner, are beneficial to the patient as they are able to take smaller of doses of the medication until the drug is efficacious. It is understandable that not all patients will require exactly the same dose of medication, for example patients of a larger build or faster metabolism and lower functional cyt. P450 broadspecific enzyme system.

Different patients may also present with different degrees of complaints and as such may require larger or smaller doses in order to treat the complaint effectively. The benefits of such a dosage form over dosage forms such as tablets, where smaller doses are difficult to take, are therefore evident.

Unit dose ranges for all formulations in the art, are preferably in the range of between 2 and 12 mg of each cannabinoid CBG, CBND and CBC with the always lower THC dose in the range of between 1 and 6 mg, more preferably in the range of 7 to 9.5 mg of each cannabinoid.

Preferably the maximum daily dosage dose of medicament is less than or equal to 120 mg CBG and less than or equal to 130 mg CBND and 130 mg CBC and less than or equal to 30 mg of THC.

Preferably the cannabinoids are packaged for delivery such that delivery is targeted to an area selected from one or more of the following: sublingual, buccal, oral, rectal, nasal and the pulmonary system.

Preferably the combination of cannabinoids is present as a *cannabis* based medicine ice cold water powder extract of the dried flower tips from specific and selected *Cannabis* varieties with high CBG and CBND and additionally a high CBD content.

More preferably the combination of cannabinoids comprises:

A *Cannabis* based medicinal extract which comprises CBG and CBND in a 1:1 ratio by weight at more than 90% of the of the total cannabinoid content in the extract (meaning that more than 90% of the total cannabinoid content is formed by the combination of CBG and CBND); and A *Cannabis* based medicinal extract which, in addition to CBG, comprises THC and CBND at more than 90% of the total cannabinoid content in the extract.

Optionally the combinations of cannabinoids are substantially pure in the oil formulations. For the *Cannabis simplex* and the trichome ice-water isolation and sieving fractions, a purity of 80% is reasonable to acquire.

Alternatively the combination of cannabinoids is synthetic.

In one embodiment the *cannabis* oils are combusted at 650-750° C. preferably at approx. at 650° C. in a cold-smoke electric device. The oil formulations are encapsulated and will consequently be evaporated inside this embodiment.

In one embodiment the trichome fraction are produced from plant material by centrifugation of the dried *Cannabis* flowers in ice-cold water. Sieving the supernatant, results in globular trichome heads (crystals, surrounded by a natural glucane/cellulose layer). This will eventually result in a white dry powder.

In one embodiment a sleep inducing *Cannabis flos* variety will be placed in a so called "curing-reactor" or "fermentor". The term "*flos*" referred to the dried flower tips of a particular *Cannabis* strain, plant, variety or chemovar (=chemotype). In this embodiment the flowers will be cured due to oxygen and temperature of about 60 to 80° C. and a duration of 2 weeks. The resulting cannabinoid profile will be changed into a more sleep inducing *Cannabis simplex* strain.

Alternatively synthetic or highly purified isolates of the cannabinoids can be used. The combination of cannabinoids may be administered in combination with one or more other drugs.

More preferably the combination of cannabinoids are administered in addition to one or more (non-cannabinoid) sleep inducing drugs or sedatives.

More preferably in combination of cannabinoids are administered separately, simultaneously or sequentially to the one or more other (non-cannabinoid) drugs.

The term "in combination" refers to administration of the cannabinoids at the same time and in the same formulation as the additional drugs.

The invention also provides a method of a trichome ice-cold water extraction and sieving of the supernatant and mixed debris. Resulting in a head (crystal) fraction, and head and stalked glandular trichome; a whole trichome-fraction. Both are used as the pharmaceutical formulation or dosage forms.

The invention makes for instance use of the following three methods of administrations:
1. Administered as *Cannabis simplex* per 50 mg unit dose for self titration.
2. Administered as powder in a tea potion hot-water based manner or preferable vapor.
3. Administered as isolated corresponding cannabinoid oils in titratable formulation in capsules with a unit dose of 0.2 mg-2 mg for vapor at 650-720° C. or 1 to 5 mg of CBG in edible form (food supplement pure sang).

EXAMPLES

Examples of Suitable Formulations

Example A: a pharmaceutical composition of CBG in a 50-120 mg unit dose.

Example B: a pharmaceutical composition of CBG in a 50-120 mg unit dose and CBND in a 50-130 mg unit dose, wherein the weight ratio of CBG:CBND is between 10:1 and 1:10.

Example C: a pharmaceutical composition of CBG in a 50-120 mg unit dose and THC in a 20-80 mg unit dose, wherein the weight ratio between CBG and THC is between 10:1 and 1:10.

Example D: a pharmaceutical composition of CBG in a 50-120 mg unit dose and CBND in a 50-130 mg unit dose and THC in a 20-80 mg unit dose, wherein the weight ratio is CBG:CBND:THC is between 10:1:1-5 and 1:10:5-1. This example is the most preferred.

Preparation of a Trichome Fraction as Cannabinoid Based Medicine

*Cannabis* with specific sleep inducing profiles; high CBG high CBC and low THC (sedative, antidepressant profiles) were grown and manufactured at the Bedrocan facilities in cooperation with the University of Nijmegen (Donders institute), section pharmacognosie (Prof. Dr. Verpoorte and Dr. A. Hazekamp) and the ministry of VWS in particular the bureau of medical *Cannabis* (BMC).

*Cannabis flos* Sleep-Variant (High CBG and CBND)

Step 1 Rough Chopping

Step 2 Put in ice-cold water

Step 3 Mix thoroughly with mixer

Step 4 Sieve 12 (sieve according to US mesh standard)

Step 5 Sieve 4 &5 (sieve according to US mesh standard)

Step 6 Remaining on latter sieve: white "powder" (mainly headcells+encapsulated droplet)

Step 7 Winterisation: removes unwanted components from the crude bo-tanical extract. The first step is to dilute the crude extract in ethanol and store the mixture at the freezing point of ethanol (114.1° C.) for at least 24 hours. This prompts the removal of lipids and waxes from the extract.

Step 8 Filtration: To remove precipitates and other particulates from the extract, one can use vacuum filtration via a Buchner funnel or a plate press. The filter micron range should be 0.45 or less.

Step 9 Distillation: To produce a cannabinoid-rich distillate product, one can either short path distillation, fractional distillation or wiped film distillation.

Step 10 Dilution: The next step is to dilute the cannabinoid mixture in the appropriate solvent to bring it to a state in which it can be pumped through a centrifugal partition chromatography column.

Step 11 Filtration: One can use a vacuum filtration via a Buchner funnel or a plate press to remove precipitates from the diluted sample solution. The filter micron range should be 0.45 or less. Now, the ex-tract is ready to be injected onto a CPC column.

CPC Process

Separating and/or purifying cannabinoids, comprising at least one liquid-liquid partition chromatography step, or the use of a centrifugal distribution chromatograph for liquid-liquid partition chromatography to separate and/or purify cannabinoids using a solvent selected from cyclohexane, heptane, n-heptane, iso-heptane, octane, n-octane, iso-octane, which is kept stationary by centrifugal force and a second immiscible liquid phase can be pumped through as a mobile phase. More details can be found in WO2016135346A1. Fractionation of neutral cannabinoids by CPC using the two-phase system hexane/acetone/acetonitrile, 5:2:3 (v:v:v, solvent system 2). The CPC is operated in ascending mode, with the lower (acetonitrile-rich) phase used as stationary phase and the upper (hexane-rich) upper phase as mobile phase. Flow-rate set at 5 ml/min and rotation speed at 600 rpm. The volume of stationary phase at 65 ml. Dissolve sample to a final volume of 5 ml of upper phase for injection. Fraction size are collected. Analyses of fractions by TLC and further analysis by HPLC. Resulting Fraction contains a high proportion (>90%) of the desired compound. This method is described in Hazekamp et al., *Preparative Isolation of Cannabinoids from Cannabis sativa by Centrifugal Partition Chromatography*, Journal of Liquid Chromatography & Related Technologies 27(15): 2421-2439—December 2004.

The resulting extract is referred to as the trichomic fraction, tea formulation or for tea potion based administration. The trichomes added to hot water behave as a colloidal solution where no precipitation of the globular trichomic particles occur.

Oil Preparation

*Cannabis flos* Sleep-Variant (High CBG)

Step 1 Chopping to predominanantly 2-3 mm;
Step 2 Decarboxylate at 150° C. for 4 minutes to form neutral (i.e. not acidic or basic) forms;
Step 3 Extraction with a specific volume of Ethanol;
Step 4 Removal by film-rotavoparization or depressuration of $CO_2$ resp.;
Step 5 Winterisation followed by chilling (−20 C/48 hr);
Step 6 Removal of unwanted waxes by cold filtration;
Step 7 Removal of ethanol from the filtrate by thin film evaporation under reduced pressure.

Winterisation removes unwanted components from the crude bo-tanical extract. The first step is to dilute the crude extract in ethanol and store the mixture at the freezing point of ethanol (114.1° C.) for at least 24 hours. This prompts the removal of lipids and waxes from the extract.

In filtration, to remove precipitates and other particulates from the extract, one can use vacuum filtration via a Buchner funnel or a plate press. The filter micron range should be 0.45 or less.

Preparation of a Strong Sleep Inducing Chemotype 1 Variety, Subtype: "WW" into a CBD Containing Strain by a Simple Curing Procedure Step 1: "WW" White widow" chemotype 1 subtype: "WW" Pressed and fresh *Cannabis simplex* medical grade is put into a Reaction chamber with overflow of oxygen, produced by water plants, at will be kept at a constant temperature of 65° C.-80° C. and incubated for approximately 2 weeks. The extract contains THC, CBG and CBC in weight ratios of 20:2-4:1 in a unit dose of 50 mg-120 mg.

The obtained composition was tested on male Wistar rats (n=16) in an amount of 20-50 mg/kg *cannabis* oil, the carrier oil being olive oil. It was administered by injection s.c. 4 hours before the lights-on period (i.e. at 10:00 h, the lights-on period being 14:00-02:00 h) on 4 consecutive days, followed by a rest period of 10 days and in total three test periods. Measurements were performed via analogic passive infrared detection (PIR) and implanted EEG electrodes.

Sedating effects of cannabinoids measured with EEG, EMG and an infrared detector in the Wistar rats Author(s): Hafkemeijer, A.; Glas, R. J.; Coenen, A. M. L.; Jongsma, M. L. A.; Rijn, C. M. van Publication year: 2010 In: FENS-Abstracts—abstr. no. 166.16 Eur. J. Soc. Psychol. January/2010

Further Examples

The compounds of the invention were subjected to pharmacological experiments which showed their valuable pharmacological properties in various areas. This concerns the extract as described above, containing THC, CBG and CBC in weight ratios of 20:2-4:1 in a unit dose of 50 mg-120 mg.

The toxicity of the compounds was determined on mice by intraperitoneal administration. The LD 50 ranges from 500 to 1,000 mg/kg.

Example Relating to Anxiolytic Activity

The anxiolytic activity was determined according to the eating test (R. J. Stephens, (1973), Brit. J. Pharmac., 49, 146 P). In this test, the doses which increase the food consumption of the mice vary from 0.1 to 10 mg/kg, administered intraperitoneally.

The activity of the compounds in the area of cerebral circulation was determined in the test for the hypoxia caused by pressure reduction. Mice of the CDI strain are kept in an oxygen-depleted atmosphere produced by creating a partial vacuum (190 mm of mercury, corresponding to 5.25% of oxygen). The survival time of the animals is noted. This time is increased by agents which are capable of assisting the oxygenation of tissues and in particular of the brain. The compounds studied are administered intraperitoneally in several doses, 10 minutes before the experiment. The percentage increases in the survival time, relative to the values obtained for control animals, are calculated. The mean active dose (MAD), that is to say the dose which increases the survival time by 100%, is determined graphically. The MAD ranges from 0.3 to 32 mg/kg, administered intraperitoneally.

Example Relating to Anticonvulsant Activity

The anticonvulsant activity was determined in accordance with the test for the antagonism towards the mortality induced by bicuculline in mice (P. Worms, H. Depoortere and K. G. Lloyd, (1979) Life Sci., 25, 607-614). The products to be studied are injected intraperitoneally, 30 minutes before the bicuculline (0.9 mg/kg, administered intravenously). With death being the criterion selected for this test, the percentage mortalities are noted for each batch, 2 hours after administration of the bicuculline (control batch: 100% mortality). For each product, the 50% active dose (AD 50 or the dose which protects 50% of the animals from the lethal effects of the bicuculline) is determined graphically. The AD 50 of the compounds of the invention vary between 0.3 and 30 mg/kg, administered intraperitoneally.

Example Relating to Sedative or Hypnotic Activity

The sedative or hypnotic activity was determined by observing the action of the compounds on the EEG of curarised rats and also on the wake-sleep states in freely moving, implanted rats and cats (H. Depoortere, Rev. E.E.G. Neurophysiol., (1980) 10, 3, 207-214; L. M. Da Costa, H. Depoortere and R. Naquet, Rev. E.E.G. Neurophysiol., (1977), 7, 2, 158-164). In curarised rats, the products to be studied were injected intraperitoneally or orally at doses increasing from 0.1 to 30 mg/kg. They induce sleep traces starting from doses ranging from 0.1 to 10 mg/kg, administered intraperitoneally or orally. In freely moving, implanted rats, the products to be studied were injected intraperitoneally or orally at a single dose ranging from 1 to 10 mg/kg. At these doses, they reduce the total wake time by 13 to 44%, without significantly changing the total paradoxical sleep time, certain products even increasing the total duration of this phase of sleep. In freely moving, implanted cats, the products to be studied were injected intraperitoneally or orally at a single dose of 10 mg/kg. They transitorily increase the wake time after injection, this being accompanied by benzodiazepine-type jactation, and reduce the total paradoxical sleep time by 40 to 100%. However, certain products increase the total duration of the SWSP (slow-wave sleep with phase phenomena: P.G.O. points) by about 50%.

Results

The results of these various tests show that the compounds of the invention possess anxiolytic, anti-anoxic, sleep-inducing, hypnotic and anticonvulsant properties; the compounds of the invention are useful for the treatment of anxiety states, sleep disorders and other neurological and psychiatric complaints, for the treatment of vigilance disorders, in particular for combating behavioural disorders which can be attributed to cerebral vascular damage and to the cerebral sclerosis encountered in geriatrics, and also for the treatment of epileptic vertigo due to cranial traumatisms and for the treatment of metabolic encephalopathies.

The compounds of the invention can be presented in any form which is suitable for oral or parenteral administration, for example in the form of tablets, coated tablets, capsules, solutions to be taken orally or injected, and the like, with any suitable excipient. The daily posology can range from 0.5 to 2,000 mg.

Clauses

1. Use of at least one cannabigerol type compound or derivative in the manufacture of a medicament for the treatment of a sleep disorder in a human patient.
2. The use according to clause 1, wherein the sleep disorder to be treated is one or more of the following: morbid or clinical depression, unipolar sleep disorder, bipolar sleep disorder, syndromal depression, panic disorder and anxiety.
3. The use according to clause 2, wherein the sleep disorder to be treated is depression.
4. The use according to any one of clauses 1 to 3, wherein the at least one cannabigerol type compound or derivative thereof is an extract from a *cannabis* plant.
5. The use according to clause 4, wherein the extract from the *cannabis* plant comprises all of the naturally occurring cannabinoids and other non-cannabinoid components that are co-extracted with the at least one cannabigerol type compound or derivative thereof.
6. The use according to clause 4, wherein the extract from the *cannabis* plant is enriched for cannabigerol.
7. The use according to clause 4, wherein the *cannabis* plant extract contains greater than or equal to 80% (w/w) cannabigerol of the total cannabinoid content.
8. The use according to clause 7, wherein the *cannabis* plant extract contains greater than or equal to 90% (w/w) cannabigerol of the total cannabinoid content.
9. The use according to clause 8, wherein the *cannabis* plant extract contains greater than or equal to 95% (w/w) cannabigerol of the total cannabinoid content.
10. The use according to clause 9, wherein the *cannabis* plant extract contains greater than or equal to 99% (w/w) cannabigerol of the total cannabinoid content.
11. The use according to any one of clauses 1 to 3, wherein the at least one cannabigerol type compound or derivative thereof is isolated or substantially pure.
12. The use according to any one of clauses 1 to 11, wherein the medicament is formulated for delivery nasally, sublingually, buccally, topically, orally, rectally, intravenously, intra-peritoneally, intramuscularly, subcutaneously, transdermally, intra-vaginally, intra-urethrally, by nebuliser, as inhaled vapour or by installation into the bladder.
13. The use according to any one of clauses 1 to 12, wherein a unit dosage form of the medicament comprises at least one cannabigerol type compound or derivative thereof in an amount of from 0.1 to 1000 mg.
14. The use according to any one of clauses 1 to 13, wherein the medicament further comprises one or more additional cannabinoids.
15. The use according to clause 14, wherein the additional cannabinoid is cannabidiol (CBD).
16. The use according to clause 14, wherein the additional cannabinoid is cannabichromene (CBC).
17. The use according to any one of the preceding clauses, wherein the at least one cannabigerol type compound or derivative is cannabigerol (CBG).
18. The use according to any one of the preceding clauses, wherein the at least one cannabigerol type compound or derivative is cannabigerol propyl analogue (CBGV).
19. The use according to any one of the preceding clauses, wherein the at least one cannabigerol type compound or derivative is cannabigerol-dimethyl heptyl.
20. The use according to any one of the preceding clauses, wherein the at least one cannabigerol type compound or derivative is cannabigerol (CBG).
21. The use according to any one of the preceding clauses, wherein the at least one cannabigerol type compound or derivative is cannabigerol propyl analogue (CBGV).
22. The use according to any one of the preceding clauses, wherein the at least one cannabigerol type compound or derivative is cannabigerol-dimethyl heptyl.
23. A method of treating a sleep disorder in a human patient which comprises administering to a patient in need thereof a therapeutically effective amount of at least one cannabigerol type compound or derivative.
24. The method according to clause 1, wherein the sleep disorder to be treated is one or more of the following: morbid or clinical depression, unipolar sleep disorder, bipolar sleep disorder, syndromal depression, panic disorder and anxiety.
25. The method according to clause 2, wherein the sleep disorder to be treated is depression.
26. The method according to clause 1, wherein the at least one cannabigerol type compound or derivative thereof is an extract from a *cannabis* plant.
27. The method according to clause 4, wherein the extract from the *cannabis* plant comprises all of the naturally occurring cannabinoids and other non-cannabinoid components that are co-extracted with the at least one cannabigerol type compound or derivative thereof.
28. The method according to clause 4, wherein the extract from the *cannabis* plant is enriched for cannabigerol.

29. The method according to clause 1, wherein the *cannabis* plant extract contains greater than or equal to 80% (w/w) cannabigerol of the total cannabinoid content.
30. The method according to clause 7, wherein the *cannabis* plant extract contains greater than or equal to 90% (w/w) cannabigerol of the total cannabinoid content.
31. The method according to clause 8, wherein the *cannabis* plant extract contains greater than or equal to 95% (w/w) cannabigerol of the total cannabinoid content.
32. The method according to clause 9, wherein the *cannabis* plant extract contains greater than or equal to 99% (w/w) cannabigerol of the total cannabinoid content.
33. The method according to clause 1, wherein the at least one cannabigerol type compound or derivative thereof is isolated or substantially pure.
34. The method according to clause 1, wherein the pharmaceutical formulation is formulated for delivery nasally, sublingually, buccally, topically, orally, rectally, intravenously, intra-peritoneally, intra-muscularly, subcutaneously, transdermally, intra-vaginally, intra-urethrally, by nebuliser, as inhaled vapour or by installation into the bladder.
35. The method according to clause 1, wherein a unit dosage form comprises at least one cannabigerol type compound or derivative thereof in an amount of 0.1 to 1000 mg.
36. A method of treating a sleep disorder in a human patient which comprises administering to a patient in need thereof a therapeutically effective amount of at least one cannabigerol type compound or derivative, wherein the pharmaceutical formulation further comprises one or more additional cannabinoids.
37. The method according to clause 14, wherein the one or more additional cannabinoids is cannabidiol (CBD).
38. The method according to clause 14, wherein the one or more additional cannabinoids is cannabichromene (CBC).
39. The method according to clause 1, wherein the at least one cannabigerol type compound or derivative is cannabigerol (CBG).
40. The method according to clause 1, wherein the at least one cannabigerol type compound or derivative is cannabigerol propyl analogue (CBGV).
41. The method according to clause 1, wherein the at least one cannabigerol type compound or derivative is cannabigerol-dimethyl heptyl.
42. The method according to clause 14, wherein the at least one cannabigerol type compound or derivative is cannabigerol (CBG).
43. The method according to clause 14, wherein the at least one cannabigerol type compound or derivative is cannabigerol propyl analogue (CBGV).
44. The method according to clause 14, wherein the at least one cannabigerol type compound or derivative is cannabigerol-dimethyl heptyl.

Further Clauses

1. The use of cannabigerol (CBG) in the manufacture of a pharmaceutical formulation for use in the treatment of chronic insomnia wherein the ratio of CBG:CBND by weight is between 10:1 and 1:10.
2. The use of sole cannabinoid Cannabigerol (CBG) in the manufacture of a pharmaceutical formulation are for use in the treatment of sleeplessness and "staying in sleep" discomfort.
3. The use of a combination of cannabinoids Cannabigerol (CBG) and Cannabinodiol (CBND) in the manufacture of a pharmaceutical formulation for use in the treatment of chronic insomnia wherein the ratio of CBG:CBND by weight is between 10:1 and 1:10.
4. The use of a combination of cannabinoids Cannabigerol (CBG) and cannabidiol (CBD) in the manufacture of a pharmaceutical formulation for use in the treatment of insomnia and insomnia related symptoms and depression.
5. The use of a combination of cannabinoids Cannabigerol (CBG) and Cannabinodiol (CBND) in the manufacture of a pharmaceutical formulation for use in the treatment of insomnia and insomnia related symptoms.
6. The use of a combination of cannabinoids Cannabigerol (CBG) and Cannabinodiol (CBND) and tetrahydrocannabinol (THC) in the manufacture of a pharmaceutical formulation for use in the treatment of insomnia, anxiety, anti-depressive, hyperactivity and insomnia related symptoms formulations with defined weight ratios of the cannabinoids cannabigerol (CBG) and cannabinodiol (CBND) and THC, wherein the ratio of CBG:CBND:THC by weight is between 10-1:1-5:1-5 or: 1-10:5-1:5-1 respectively; ore preferably the ratio for *Cannabis simplex* is 4-10% THC and 3-10% of CBG and 3-10% of CBND (strong formulation; CBG:CBND:THC of 3-10:10-3:4-1, 1-4 for TCF and oil formulations.
7. The use of a combination of cannabinoids Cannabigerol (CBG), Cannabinodiol (CBND) and cannabichromene (CBC) in the manufacture of a pharmaceutical formulation for use in the treatment of insomnia, anxiety, hyperactivity, anti-depressive and insomnia related symptoms.
8. The use of a combination of cannabinoids Cannabigerol (CBG), Cannabinodiol (CBND), cannabichromene (CBC) and tetrahydrocannabinol (THC) in the manufacture of a pharmaceutical formulation for use in the treatment of insomnia, anxiety, hyperactivity, as anti-depressive and insomnia related symptoms.
9. The use of cannabinoids in the manufacture of a pharmaceutical formulation with CBG and THC only are for use in the treatment of depression as anti-depressive and a remedy for a depressive mood wherein the ratio of CBG: and THC by weight is between 10:1 and 1:10. preferably between 1:5 and 5:1.
10. The use of cannabinoids in the manufacture of a pharmaceutical formulation are for use in the treatment of hyperactivity.
11. The use of cannabinoids in the manufacture of a pharmaceutical formulation are for use as mood stabilizer and relaxator, wherein the ratio of CBG:THC by weight is between 7:3 and 3:7. preferably between 2:5 and 5:2.
12. The use of the cannabinoids according to clause 1 in the manufacture of a pharmaceutical formulation are for use in the treatment of improving subjective and objective sleep disorders, primary and secondary sleep disorders.
13. The use of the cannabinoids according to clauses 1 to 11 in the manufacture of a pharmaceutical formulation, wherein the cannabinoids are packaged for delivery in a titratable dosage form.
14. The use of the cannabinoids according to clauses 1 to 12 in the manufacture of a pharmaceutical formulation, wherein the cannabinoid CBG is administered separately, simultaneously or sequentially tot the cannabinoid CBND or CBC or THC.
15. The use of the cannabinoids according to clauses 1 to 13 in the manufacture of a pharmaceutical formulation, wherein the cannabinoids are packaged for delivery in a titratable dosage form.

16. The use of the cannabinoids according to clauses 1 to 14 in the manufacture of a pharmaceutical formulation, wherein a unit dose taken by a patient is in the range of 2-12 mg of each cannabinoid.

17. The use of the cannabinoids according to clause 14 in the manufacture of a pharmaceutical formulation, wherein a unit dose taken by a patient is in the range of 7-8.5 mg of each cannabinoid.

18. The use of the cannabinoids according to clause 1 to 16 in the manufacture of a pharmaceutical formulation, wherein the maximum daily dosage of each cannabinoid is less than or equal to 120 mg of CBG and less than or equal to 130 mg of CBND.

19. The use of the cannabinoids according to clause 4 and 5 in the manufacture of a pharmaceutical formulation, wherein the maximum daily dosage of each cannabinoid is less than or equal to 120 mg of CBG and less than or equal to 130 mg of CBND.

20. The use of the cannabinoids according to clause 6, 7, 8 and 9 to 12 in the manufacture of a pharmaceutical formulation, wherein the maximum daily dosage of each cannabinoid is less than or equal to 120 mg of CBG and less than or equal to 130 mg of CBND and 120 mg, 20-80 mg of THC and 130 mg of CBC.

21. The use of the cannabinoids according to clauses 1 to 18 in the manufacture of a pharmaceutical formulation, wherein the cannabinoids are packaged for delivery such that delivery is targeted to an area selected from the group consisting of: sublingual, buccal, oral, rectal, nasal and the pulmonary system.

22. The use of the cannabinoids according to clause 17 in the manufacture of a pharmaceutical formulation, wherein the cannabinoids are in the form selected from the group consisting of: gel, gel spray, tablet, liquid, capsule, for vaporization and for nebulisation.

23. The use of the cannabinoids according to clauses 1 to 20 in the manufacture of a pharmaceutical formulation, wherein the combination of cannabinoids comprises:
 A *Cannabis* based medicinal extract which comprises CBG and CBND in a 1:1 ratio by weight at more than 90% of the of the total cannabinoid content in the extract; and
 A *Cannabis* based medicinal extract which comprises CBG at more than 90% of the total cannabinoid content in the extract;
 A *Cannabis* based medicinal extract which comprises THC and CBND in a 1:1 ratio at more than 90% of the total cannabinoid content in the extract;
 A *Cannabis* based medicinal extract which comprises CBG, THC and CBND in a 1:1:1 ratio, at more than 90% of the total cannabinoid content in the extract;
 A *Cannabis* based medicinal extract which comprises THC and CBND in a ratio of weight 1:1: at more than 90% of the total cannabinoid content in the extract;
 A *Cannabis* based medicinal extract which comprises CBG, CBD, THC and CBND in a 1:1:1:1 ratio, at more than 90% of the total cannabinoid content in the extract.

24. The use of the cannabinoids according to clauses 1 to 13 wherein the cannabinoids are synthetic.

25. The use of the cannabinoids according to clauses 1 to 23 in the manufacture of a pharmaceutical formulation, wherein the cannabinoids are administered in combination with one or more other drugs.

26. The use of the cannabinoids according to clause 25 in the manufacture of a pharmaceutical formulate on, wherein the cannabinoids are administered in addition to one or more synthetic sedatives or sleeping pills.

27. A method of treating insomnia and all related sleep disorders according to clause 1 in a human subject in need thereof a therapeutically effective amount of a combination of cannabinoids cannabigerol (CBG) alone, and CBG plus cannabinodiol (CBND), wherein the ratio of CBG and CBND by weight is between 10:1 and 1:10.

28. A method of treating depression, depressive modes and anxiety in a human subject in need thereof a therapeutically effective amount of a combination of cannabinoids cannabigerol (CBG) alone, and CBG plus cannabinodiol (CBND), wherein the ratio of CBG and CBND by weight is between 10:1 and 1:10 and CBG and THC wherein the ratio of CBG and THC by weight is between 5:1 and 1:5

29. A method of hyperactivity and as relaxant in a human subject in need thereof a therapeutically effective amount of a combination of cannabinoids cannabigerol (CBG) alone, and CBG plus cannabinodiol (CBND), wherein the ratio of CBG and CBND by weight is between 10:1 and 1:10 and CBG and THC wherein the ratio of CBG and THC by weight is between 5:1 and 1:5.

30. A method according to clauses 27 to 29 wherein the combination of cannabinoids cannabigerol (CBG), cannabidiol (CBND) and CBC and THC is present in a pharmaceutical formulation as defined in any one of clauses 9 to 26.

The invention claimed is:

1. A composition comprising a mixture of cannabinoids for use in the treatment of chronic insomnia, sleeplessness and "staying in sleep" discomfort, subjective and objective sleep disorders, primary and secondary sleep disorders, insomnia related symptoms, depression, anxiety, and/or hyperactivity,
 wherein the mixture of cannabinoids is cannabigerol (CBG), cannabinodiol (CBND), and tetrahydrocannabinol (THC),
 wherein the mixture of cannabinoids has a weight ratio of CBG:CBND:THC between 10-1:1-5:1-5 or between 1-10:5-1:5-1, wherein the composition further comprises cannabinoid cannabichromene (CBC).

2. The composition of claim 1, wherein the ratio of CBG:THC by weight is between 7:3 and 3:7.

3. The composition of claim 1, wherein said CBG is administered separately, simultaneously or sequentially to said CBND.

4. The composition of claim 1, wherein the maximum daily dosage of CBG is less than or equal to 120 mg.

5. The composition of claim 1, wherein the maximum daily dosage of cannabinoids is less than or equal to 130 mg of CBND, less than or equal to 20-80 mg of THC and less than or equal to 130 mg of CBC.

6. The composition of claim 1, wherein the mixture of cannabinoids is packaged for delivery such that delivery is targeted to an area selected from the group consisting of: sublingual, buccal, oral, rectal, nasal and the pulmonary system.

7. The composition of claim 1, wherein the mixture of cannabinoids is in the form selected from the group consisting of: gel, gel spray, tablet, liquid, capsule, for vaporization and for nebulisation.

8. The composition of claim 1,
 wherein the CBG is a synthetic form of CBG,
 wherein the CBND is a synthetic form of CBND,
 wherein the THC is a synthetic form of THC,
 wherein the CBC is a synthetic form of CBC.

9. The composition of claim 1, further comprising one or more synthetic sedatives or one or more sleeping pills, wherein the mixture of cannabinoids is for administration in combination with the one or more synthetic sedatives or the one or more sleeping pills, wherein the one or more synthetic sedatives or sleeping pills are independently selected from zolpidem and pyrazolopyrimidine.

10. The composition of claim 1, wherein said CBG is administered separately, simultaneously or sequentially to said CBC.

11. The composition of claim 1, wherein said CBG is administered separately, simultaneously or sequentially to said THC.

* * * * *